US012773416B2

(12) United States Patent
Mayberry et al.

(10) Patent No.: US 12,773,416 B2
(45) Date of Patent: Oct. 27, 2026

(54) COMPOSITION, ARTICLE AND METHOD FOR AFFECTING A MAMMAL

(71) Applicant: COOLHOUSE SOURCING LLC, Minneapolis, MN (US)

(72) Inventors: Lee Wayne Mayberry, Arvada, CO (US); Matthew David Scarlett, Edina, MN (US); Max Runke, Minneapolis, MN (US)

(73) Assignee: Coolhouse Resourcing LLC, Minneapolis, MN (US)

( * ) Notice: Subject to any disclaimer, the term of this patent is extended or adjusted under 35 U.S.C. 154(b) by 620 days.

(21) Appl. No.: 17/971,462

(22) Filed: Oct. 21, 2022

(65) Prior Publication Data

US 2023/0056488 A1 Feb. 23, 2023

Related U.S. Application Data

(63) Continuation of application No. PCT/US2021/028302, filed on Apr. 21, 2021.

(60) Provisional application No. 63/013,158, filed on Apr. 21, 2020.

(51) Int. Cl.

| | |
|---|---|
| *A61K 31/00* | (2006.01) |
| *A61K 9/00* | (2006.01) |
| *A61K 31/10* | (2006.01) |
| *A61K 31/197* | (2006.01) |
| *A61K 31/198* | (2006.01) |
| *A61K 31/405* | (2006.01) |
| *A61K 36/185* | (2006.01) |
| *A61K 36/258* | (2006.01) |
| *A61K 36/324* | (2006.01) |
| *A61K 36/81* | (2006.01) |
| *A61K 36/9066* | (2006.01) |

(52) U.S. Cl.

CPC .......... *A61K 31/658* (2023.05); *A61K 9/0056* (2013.01); *A61K 9/006* (2013.01); *A61K 31/10* (2013.01); *A61K 31/197* (2013.01); *A61K 31/198* (2013.01); *A61K 31/405* (2013.01); *A61K 36/258* (2013.01); *A61K 36/324* (2013.01); *A61K 36/3482* (2024.05); *A61K 36/81* (2013.01); *A61K 36/9066* (2013.01)

(58) Field of Classification Search

None

See application file for complete search history.

(56) References Cited

U.S. PATENT DOCUMENTS

| | | | | |
|---|---|---|---|---|
| 8,609,162 | B2 | 12/2013 | Giuliano et al. | |
| 10,080,736 | B2 | 9/2018 | Kleidon et al. | |
| 10,201,553 | B1 | 2/2019 | Steinberg et al. | |
| 10,434,061 | B2 | 10/2019 | Singer | |
| 10,517,322 | B1 | 12/2019 | Lee | |
| 2004/0138293 | A1* | 7/2004 | Werner | A61K 31/352 514/454 |
| 2008/0033027 | A1 | 2/2008 | Bascomb et al. | |
| 2011/0064712 | A1 | 3/2011 | Amato | |
| 2011/0223150 | A1 | 9/2011 | Halloway | |
| 2015/0320814 | A1 | 11/2015 | Patel et al. | |
| 2017/0065654 | A1 | 3/2017 | Rubin | |
| 2017/0172977 | A1 | 6/2017 | Kleidon et al. | |
| 2017/0188616 | A1 | 7/2017 | Alfiere et al. | |
| 2018/0169069 | A1 | 6/2018 | Bascomb et al. | |
| 2018/0339008 | A1 | 11/2018 | Klele | |
| 2018/0360739 | A1 | 12/2018 | Lorenz et al. | |
| 2019/0046440 | A1 | 2/2019 | Kleidon et al. | |
| 2019/0060225 | A1* | 2/2019 | Mandel | A23L 33/105 |
| 2019/0336471 | A1 | 11/2019 | DeMarco et al. | |
| 2019/0336472 | A1 | 11/2019 | Leone-Bay et al. | |
| 2020/0078332 | A1 | 3/2020 | Leone-Bay et al. | |

FOREIGN PATENT DOCUMENTS

| | | |
|---|---|---|
| EP | 0358536 | 5/1996 |
| EP | 2598122 | 9/2015 |
| WO | WO 2018/112138 | 6/2018 |
| WO | WO 2018/175992 | 9/2018 |
| WO | WO 2019/056129 | 3/2019 |
| WO | WO 2019/071211 | 4/2019 |
| WO | WO 2019/071213 | 4/2019 |
| WO | WO 2019/126184 | 6/2019 |
| WO | WO 2019/140406 | 7/2019 |
| WO | WO 2019/195943 | 10/2019 |
| WO | WO 2020/009950 | 1/2020 |

OTHER PUBLICATIONS

Fisar (Inhibition of monoamine oxidase activity by cannabinoids, Naunyn Schmiedebergs Arch Pharmacol, Jun. 2010; 381(6):563-72).*

FOMO Bones, "CBD Dog treats for the anxious dog," 2018, 13 pages.

Head et al., "Nutrients and botanicals for treatment of stress: adrenal fatigue, neurotransmitter imbalance, anxiety, and restless sleep," 2009, 27 pages.

Levine et al., "S-adenosyl-l-methionine (SAMe), cannabidiol (CBD), and kratom in psychiatric disorders: clinical and mechanistic considerations," Brain, Behavior, and Immunity, 2019, 10 pages.

(Continued)

*Primary Examiner* — Melissa S Mercier

(74) *Attorney, Agent, or Firm* — Husch Blackwell LLP

(57) ABSTRACT

Compositions, articles and methods for treating sleeplessness, anxiety, pain or inflammation include: (i) one or more pharmacologically active, non-psychoactive cannabinoids; (ii) one or more active agents; and an optional carrier or matrix. The optional carrier or matrix may comprise ingredients such as solvents, solid or dissolvable supports, fillers, flavorants, flavor or taste masking agents, and other adjuvants that provide the composition in a useful form factor configured for easy administration to a mammal of an appropriate pharmacological dosage of the active ingredients.

22 Claims, 2 Drawing Sheets

(56) References Cited

OTHER PUBLICATIONS

"SHODEN," retrieved from the Internet: <www.nutriscienceusa.com/branded-ingredients/shoden-ashwagandha>, retrieved on Oct. 21, 2022, 4 pages, 2021.
Weeks, Formulations of dietary supplements and herbal extracts for relaxation and anxiolytic action: RelarianTM, Med Sci Monit, 2009, 15(11): RA256-262.
Mischoulon and Fava, "Role of S-adenosyl-L-methionine in treatment of depression: a review of evidence," Am J Clin Nutr. 2002:76(5):1158S-1161S.
Ravindran et al., "Complementary and alternative therapies as add-on to pharmacotherapy for mood and anxiety disorders: a systematic review," J Affect Disord., 2013, 150:707-19 (Abstract).
Young, "Clinical nutrition: 3. The fuzzy boundary between nutrition and psychopharmacology," CMAJ, 2002, 5 pages.
Young, "The use of diet and dietary components in the study of factors controlling affect in humans: a review," J Psychiatry Neurosci., 1993, 18(5):235-244.
International Preliminary Report on Patentability for International Application No. PCT/US 2021/028302, dated Oct. 25, 2022, 9 pages.

* cited by examiner

COMPOSITION, ARTICLE AND METHOD FOR AFFECTING A MAMMAL

CROSS REFERENCE TO RELATED APPLICATIONS

This application is a continuation under 35 U.S.C. § 111 of International Application No. PCT/US2021/028302 filed Apr. 21, 2021, which claims priority under 35 U.S.C. § 119 to U.S. Provisional Application No. 63/013,158 filed Apr. 21, 2020, the disclosures of both of which are incorporated herein by reference.

BACKGROUND

Many people find it hard to achieve a good night's sleep. Some turn to sleep aid compositions. Prescription sleep medicines have numerous side effects, including being addictive or leaving the user feeling drowsy or hung over in the morning. Other reported side effects of prescription sleep medicines include burning or tingling in the hands, arms, feet, or legs; changes in appetite; constipation; diarrhea; difficulty keeping balance; dizziness; dry mouth or throat; gas; headache; heartburn; impairment the next day; mental slowing or problems with attention or memory; stomach pain or tenderness; uncontrollable shaking of one or more body parts; unusual dreams; and weakness. Non-prescription cold or headache medicines are also sometimes used as sleep aids. These remedies suffer their own set of reported deficiencies, including being ineffective or leaving the person with a morning hangover, dry nose and mouth, etc.

Episodic anxiety (or anxiousness) impacts mammals of all kinds, including, for example, people, dogs, horses and other animals. For example, some dogs may become extremely agitated when their owner leaves them alone, e.g., to go to work or on an errand. Dogs can also become agitated when exposed to noises such as thunder, construction equipment, etc.

Pain and inflammation also impact mammals of all kinds. In addition to the discomfort caused by the pain or inflammation, these issues may contribute to the mammal's anxiety and sleeplessness.

From the foregoing, it will be appreciated that what is needed in the art is a non-addictive but effective treatment for one or more issues including sleeplessness, anxiety, pain and inflammation. Such systems and methods are disclosed and claimed herein.

SUMMARY

Various aspects of the instant disclosure are directed to compositions, systems or methods that provide health or wellness benefits to mammals. As will be apparent from the more detailed discussion that follows, one or more these aspects are directed to overcoming issues including but not limited to those mentioned above.

The present invention provides, in one aspect, a composition for treating sleeplessness, anxiety, pain or inflammation in a mammal, the composition comprising one or more active ingredients selected from the following classes:

(i) pharmacologically active, non-psychoactive cannabinoids (e.g., cannabidiol or "CBD"); and (ii) pharmacologically active, non-prescription, non-cannabinoid active agents from the following subclasses:

a) amino acid-based ingredients having central nervous system effects;

b) receptor modulators for acetylcholinesterase, butyrylcholinesterase, 5-HT1 or 5-HT2; and c) extracts or ground portions (other than such receptor modulators) of a medicinal plant, tree bark or roots; and an optional carrier or matrix in which the active ingredients are dissolved or dispersed. In a further embodiment, the disclosed composition is in the form of an article comprising a carrier or matrix in which active ingredients (i) and (ii) are dispersed. The invention provides, in yet another aspect, a method for treating sleeplessness, anxiety, pain or inflammation in a mammal, the method comprising the step of administering to such mammal the aforementioned composition.

The present invention provides, in another aspect, a composition for treating sleeplessness, anxiety, pain or inflammation in a mammal, the composition comprising as active ingredients:

(i) one or more pharmacologically active, non-psychoactive cannabinoids; and (ii) a pharmacologically active, non-prescription, non-cannabinoid active agent from each of the following subclasses:

a) amino acid-based ingredients having central nervous system effects;

b) receptor modulators for acetylcholinesterase, butyrylcholinesterase, 5-HT1 or 5-HT2; and c) extracts or ground portions (other than such receptor modulators) of a medicinal plant, tree bark or roots; and an optional carrier or matrix in which the active ingredients are dissolved or dispersed. In a further embodiment, the disclosed compositions further comprise a nonprescription active agent from the following subclass:

d) monoamine metabolizers.

The disclosed optional carrier or matrix may comprise a solvent, dispersing liquid, dissolvable support, solid support, filler, flavorant, flavor or taste masking agent, and other adjuvants that provide the composition in a useful form factor configured for easy administration to a mammal of an appropriate pharmacological dosage of the active ingredients.

The invention provides, in another aspect, an article for treating sleeplessness, anxiety, pain or inflammation in a mammal, the article comprising the following ingredients:

(i) one or more pharmacologically active, non-psychoactive cannabinoids; and (ii) a pharmacologically active, non-prescription, non-cannabinoid active agent from each of the following subclasses:

a) amino acid-based ingredients having central nervous system effects;

b) receptor modulators for acetylcholinesterase, butyrylcholinesterase, 5-HT1 or 5-HT2; and c) extracts or ground portions (other than such receptor modulators) of a medicinal plant, tree bark or roots; and (iii) a carrier or matrix in which active ingredients (i) and (ii) are dispersed.

In a further embodiment, the disclosed articles further comprise a nonprescription active agent from the following subclass:

d) monoamine metabolizers.

The invention provides, in yet another aspect, a method for treating sleeplessness in a mammal, the method comprising the step of administering to such mammal a composition comprising as active ingredients:

(i) one or more pharmacologically active, non-psychoactive cannabinoids; and (ii) a pharmacologically active, non-prescription, non-cannabinoid active agent from each of the following subclasses:

a) amino acid-based ingredients having central nervous system effects;

b) receptor modulators for acetylcholinesterase, butyrylcholinesterase, 5-HT1 or 5-HT2; and c) extracts or ground portions (other than such receptor modulators) of a medicinal plant, tree bark or roots; and (iii) a carrier or matrix in which active ingredients (i) and (ii) are dispersed.

The invention provides, in yet another aspect, a method for treating anxiety in a mammal, the method comprising the step of administering to such mammal a composition comprising as active ingredients:

(i) one or more pharmacologically active, non-psychoactive cannabinoids; and (ii) a pharmacologically active, non-prescription, non-cannabinoid active agent from each of the following subclasses:

a) amino acid-based ingredients having central nervous system effects;

b) receptor modulators for acetylcholinesterase, butyrylcholinesterase, 5-HT1 or 5-HT2; and c) extracts or ground portions (other than such receptor modulators) of a medicinal plant, tree bark or roots; and (iii) a carrier or matrix in which active ingredients (i) and (ii) are dispersed.

The invention provides, in yet another aspect, a method for treating pain or inflammation in a mammal, the method comprising the step of administering to such mammal a composition comprising as active ingredients:

(i) one or more pharmacologically active, non-psychoactive cannabinoids; and (ii) a pharmacologically active, non-prescription, non-cannabinoid active agent from each of the following subclasses:

a) amino acid-based ingredients having central nervous system effects;

b) receptor modulators for acetylcholinesterase, butyrylcholinesterase, 5-HT1 or 5-HT2; and c) extracts or ground portions (other than such receptor modulators) of a medicinal plant, tree bark or roots; and (iii) a carrier or matrix in which active ingredients (i) and (ii) are dispersed.

In further embodiments, the disclosed methods comprise administering to such mammal such composition, wherein the composition further comprises a nonprescription monoamine metabolizer active agent.

In further embodiments, the disclosed compositions, articles and methods are substantially free of, or completely free of, at least one, two or more, or all of:

(i) prescription drugs, (ii) over-the-counter cold remedies, (iii) over-the-counter allergy treatments, (iv) stimulants, e.g., caffeine, (when the composition is intended to treat sleeplessness), (v) psychoactive cannabinoids (e.g., tetrahydrocannabinol or "THC"), (vi) antagonists for the amino acid-based ingredients present such compositions, articles or methods, (vii) antagonists for the receptor modulators present such compositions, articles or methods, or (viii) antagonists for the extracts or ground portions of a medicinal plant, tree bark or root present such compositions, articles or methods.

The above summary is not intended to describe each disclosed embodiment or every implementation. The description that follows more particularly exemplifies illustrative embodiments.

The details of one or more embodiments of the invention are set forth in the accompanying drawing and the description below. Other features, objects, and advantages of the invention will be apparent from the description and drawing, and from the claims.

BRIEF DESCRIPTION OF THE DRAWING

The disclosure can be more completely understood in consideration of the following detailed description of various embodiments of the disclosure, in connection with the accompanying drawings, in which.

Figure 1:
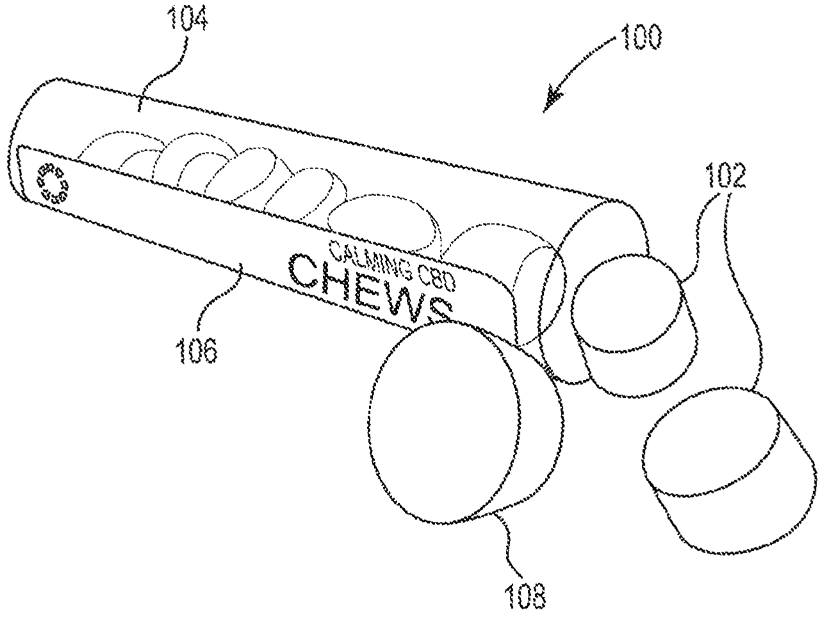
FIG. 1 is a perspective view of a packaged chew product for administration of a semisolid of solid embodiment of the disclosed composition to a person, dog, cat or other mammal.

While embodiments of the disclosure are amenable to various modifications and alternative forms, specifics thereof shown by way of example in the drawings will be described in detail. It should be understood, however, that the intention is not to limit the disclosure to the particular embodiments described. On the contrary, the intention is to cover all modifications, equivalents, and alternatives falling within the scope of the subject matter as defined by the claims.

DETAILED DESCRIPTION

Unless otherwise specified, the following terms as used herein have the meanings provided below.

Terms such as "a," "an," "the," "at least one," and "one or more" are used interchangeably. Thus, for example, a composition that comprises "an" ingredient can be interpreted to mean that the composition includes "one or more" ingredients.

The term "active ingredient" when used in connection with a chemical administered to or to be administered to a mammal means that such chemical is bioactive in such mammal.

The terms "comprises," "includes" and variations thereof do not have a limiting meaning where these terms appear in the description and claims.

The term "extract" or "ground portion" when used in connection with a medicinal plant, tree bark or root refers to a chemical or mixture of chemicals obtained from such plant by any suitable purification or concentration technique (e.g., by expression, absorption, maceration or distillation), and shall also include a synthesized (including fermented or otherwise biosynthesized) chemical or mixture of chemicals having the same or substantially pharmacologically equivalent structures.

The term "non-prescription" when used in connection with an active ingredient administered to or to be administered to a mammal means an active ingredient whose purchase or use do not require a prescription from a licensed medical doctor or veterinarian in the applicable jurisdiction where such administration occurs or will occur.

The term "non-psychoactive" when used in connection with an active ingredient administered to or to be administered to a mammal means that the ingredient does not produce a significant effect (such as changes in perception or behavior) on the mind or mental processes of such mammal. By way of example, a person having ordinary skill in the art would regard CBD as non-psychoactive and THC as psychoactive.

The term "over-the-counter cold remedies" refers to a non-prescription retail product whose primary labelled use is for the treatment of the common cold symptoms.

The term "over-the-counter allergy treatments" refers to a non-prescription retail product whose primary labelled use is for the treatment of allergy symptoms.

The term "pharmacologically active" when used in connection with an active ingredient administered to or to be administered to a mammal means that such chemical has beneficial bioactive effects.

The terms "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the invention.

In various embodiments are disclosed compositions, articles and methods for treating sleeplessness; anxiety issues; pain issues; and inflammation issues. Referring first to FIG. 1 a product 100 is shown in perspective view. Product 100 contains a plurality (eight in this instance) of bite-sized semisoft or solid chews 102 packaged in a transparent tube 104 having a label 106 bearing text depicting information such as ingredients, dosage or serving size information, usage instructions, manufacturing codes, use-by dates, product naming, product branding and other relevant matters. Cap 108 provides a recloseable seal for the open end of tube 104.

Figure 2:
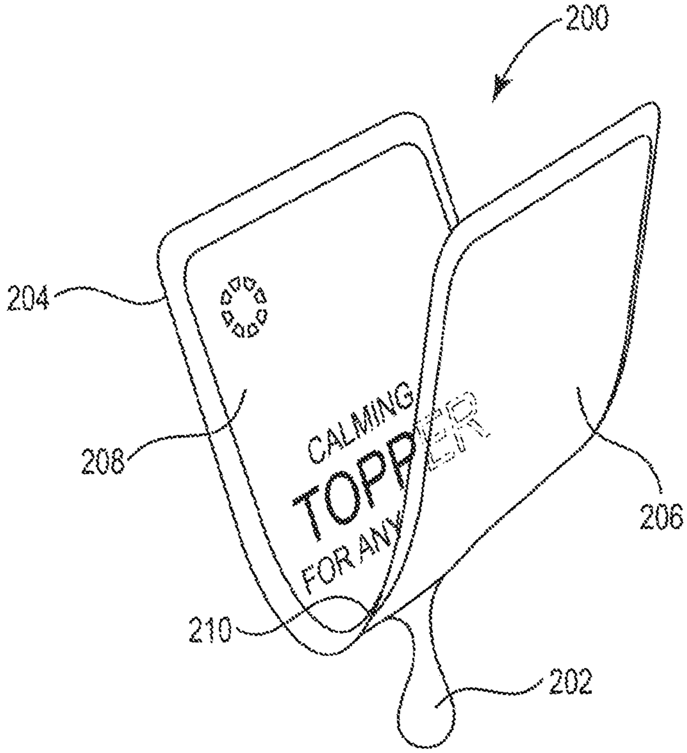
FIG. 2 is a perspective view of a packaged liquid topper product for application of a liquid embodiment of the disclosed composition to a food or beverage that will be consumed by a person, dog, cat or other mammal.

FIG. 2 shows a perspective view of a product 200 containing a single serving quantity of a liquid topper 202 that can for example be poured, dripped or squeezed from pouch 204 onto, for example, a food or beverage (not shown in FIG. 2). As depicted in FIG. 2, pouch 204 has been opened by folding it and causing stressed outwardly-facing side 206 to fracture and separate near fold 208. Inwardly-facing side 208, side 206 or both sides 206 and 208 may be printed or otherwise labeled with information such as ingredients, dosage or serving size information, opening instructions, usage instructions, manufacturing codes, use-by dates, product naming, product branding and other relevant matters. Pouch 204 is intended for one-time use and recycling or discard after it has been opened and its contents 202 removed.

Figure 3:
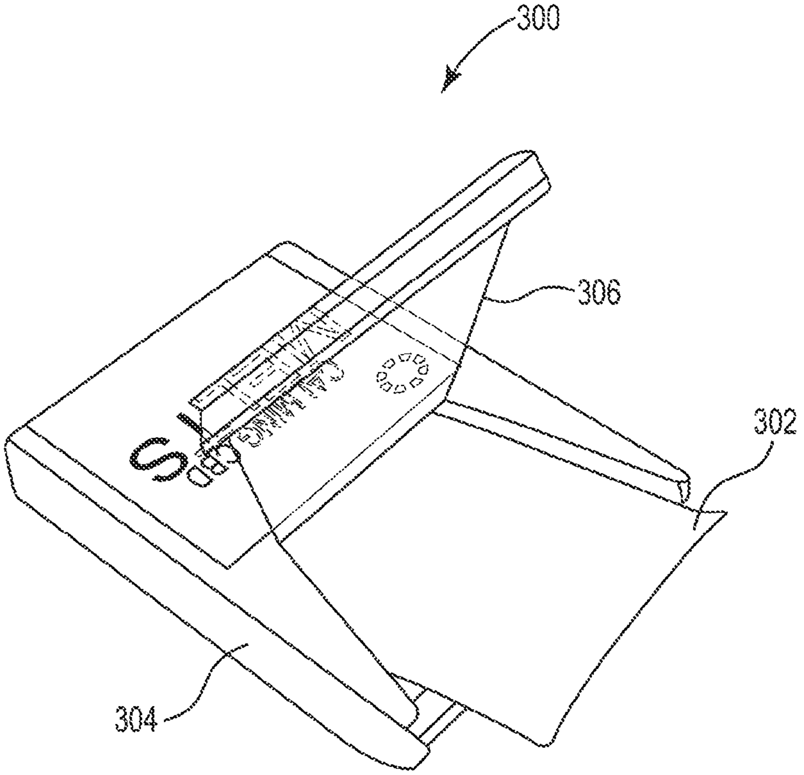
FIG. 3 is a perspective view of a packaged melt strip product for administration of another embodiment of the disclosed composition to a person, dog, cat or other mammal.

FIG. 3 shows a perspective view of a product 300 containing a plurality of flexible melt strips 302 in a translucent boxlike container 304 equipped with a hinged (and as depicted in FIG. 3, opened) recloseable flap 306 that enables individual strips 302 to be easily slid one at a time from container 304. Container 304 may be printed or otherwise labeled with information such as ingredients, dosage or serving size information, usage instructions, manufacturing codes, use-by dates, product naming, product branding and other relevant matters. One or more removed strips 302 may be placed in the mouth (e.g., on or under the tongue, or between the cheek and gum) of a user and licked, chewed or simply left in place and allowed to melt, thereby releasing the disclosed composition into the user's body.

For convenience, the above-mentioned cannabinoids and active agents will sometimes collectively be referred to as "active ingredients." A variety of active ingredients may be used in the disclosed compositions. Exemplary such active ingredients may be selected from the following classes: (i) pharmacologically active, non-psychoactive cannabinoids; and (ii) pharmacologically active, non-prescription, non-cannabinoid active agents selected from the following subclasses: (a) amino acid-based ingredients having central nervous system effects; (b) receptor modulators for acetylcholinesterase, butyrylcholinesterase, 5-HT1 or 5-HT2; and (c) extracts or ground portions (other than such receptor modulators) of a medicinal plant, tree bark or roots; and an optional carrier or matrix in which the active ingredients are dissolved or dispersed.

In a further embodiment, the disclosed composition is in the form of an article comprising a carrier or matrix in which active ingredients (i) and (ii) are dispersed. The invention provides, in yet another aspect, a method for treating sleeplessness, anxiety, pain or inflammation in a mammal, the method comprising the step of administering to such mammal the aforementioned composition or article.

Other exemplary compositions include as active ingredients: (i) one or more pharmacologically active, non-psychoactive cannabinoids; and (ii) a pharmacologically active, non-prescription, non-cannabinoid active agent from each of the following subclasses: (a) amino acid-based ingredients having central nervous system effects; (b) receptor modulators for acetylcholinesterase, butyrylcholinesterase, 5-HT1 or 5-HT2; and (c) extracts or ground portions (other than such receptor modulators) of a medicinal plant, tree bark or roots; and an optional carrier or matrix in which the active ingredients are dissolved or dispersed. In a further embodiment, the disclosed compositions further comprise a nonprescription active agent from the following subclass: (d) monoamine metabolizers.

The disclosed optional carrier or matrix may comprise a solvent, dispersing liquid, dissolvable support, solid support, filler, flavorant, flavor or taste masking agent, and other adjuvants that provide the composition in a useful form factor configured for easy administration to a mammal of an appropriate pharmacological dosage of the active ingredients.

Exemplary articles for treating sleeplessness, anxiety, pain or inflammation in a mammal include the aforementioned compositions and a carrier or matrix in which the aforementioned active ingredients are dispersed.

An exemplary method for treating sleeplessness in a mammal includes the step of administering to a mammal a composition comprising as active ingredients:

(i) one or more pharmacologically active, non-psychoactive cannabinoids; and (ii) a non-prescription, non-cannabinoid active agent from each of the following subclasses:

a) amino acid-based ingredients having central nervous system effects;

b) receptor modulators for acetylcholinesterase, butyrylcholinesterase, 5-HT1 or 5-HT2; and c) extracts or ground portions (other than such receptor modulators) of a medicinal plant, tree bark or roots; and (iii) a carrier or matrix in which active ingredients (i) and (ii) are dispersed.

An exemplary method for treating anxiety in a mammal includes the step of administering to such mammal a composition comprising as active ingredients:

(i) one or more pharmacologically active, non-psychoactive cannabinoids; and (iv) a non-prescription, non-cannabinoid active agent from each of the following subclasses:

a) amino acid-based ingredients having central nervous system effects;

b) receptor modulators for acetylcholinesterase, butyrylcholinesterase, 5-HT1 or 5-HT2; and c) extracts or ground portions (other than such receptor modulators) of a medicinal plant, tree bark or roots; and (ii) a carrier or matrix in which active ingredients (i) and (ii) are dispersed.

An exemplary method for treating pain or inflammation in a mammal includes the step of administering to such mammal a composition comprising as active ingredients:

(i) one or more pharmacologically active, non-psychoactive cannabinoids; and (v) a non-prescription, non-cannabinoid active agent from each of the following subclasses:

a) amino acid-based ingredients having central nervous system effects;

b) receptor modulators for acetylcholinesterase, butyrylcholinesterase, 5-HT1 or 5-HT2; and c) extracts or ground portions (other than such receptor modulators) of a medicinal plant, tree bark or roots; and (ii) a carrier or matrix in which active ingredients (i) and (ii) are dispersed.

Exemplary methods may further comprise administering to such mammal such composition, wherein the composition further comprises a nonprescription monoamine metabolizer active agent.

Exemplary compositions include: (i) one or more active agents; (ii) one or more cannabinoids; or (iii) a combination of one or more active agents and one or more cannabinoids. The compositions may further optionally comprise other ingredients (such as carriers, fillers, flavorants, flavor or taste masking agents, etc.) to provide the composition in a useful, palatable form factor. While a variety of forms of administration may be employed (e.g., venous or subcutaneous injection, transdermal delivery, nasal sprays or drops, ear drops, and suppositories), the disclosed compositions are preferably configured for oral administration in an easy to administer form, for delivery to a mammal of an appropriate pharmacological dosage of active ingredients.

As will be well understood in the medical and veterinary arts, the size of a mammal will often impact the suitable and preferred dosages of the various active ingredients. For that reason, it is preferable to express active ingredient dosages as milligrams of the ingredient per kilogram of the mammal's body size (viz., mg/kg). For animals such as dogs, it is common to prepare dosages for small dogs (5 to 25 pounds; 2.3 to 11.3 kg), medium dogs (26 to 50 pounds; 11.8 to 22.7 kg) and large dogs (51 to 100 pounds; 23.1 to 45.4 kg). Typically, the dosage of an ingredient will target the midpoint of the lower and upper ends of the weights for the particular size of dog. For example, a medium sized dog has an 11.8 to 22.7 kg size range, with a midpoint of 17.2 kg. When expressing dosages of an ingredient in this document, and unless otherwise specified, the stated dosage will generally refer to mg/kg.

For over the counter distribution of the disclosed compositions and articles, the preferred, more preferred and most preferred dosage ranges can be converted from the mg/kg figures recited above into mg dosage figures for each ingredient by using the following average body sizes: Small dog (6.8 kg); Medium dog (17.2 kg), Large dog (34 kg), horse (500 kg), cat (4 kg) and human (75 kg).

Exemplary cannabinoids for use in the present invention include pharmacologically active, but non-psychoactive, cannabinoids. Presently preferred cannabinoids include cannabidiol ("CBD"), cannabinol ("CBN"), cannabigerol ("CBG"), cannabichromene ("CBC"), cannabielsoin ("CBE"), cannabicyclol ("CBL"), cannabicitran ("CBT"), cannabichromanone ("CBCN"), cannabinodiol ("CBND"), Tetrahydrocannabivarin ("THCV") and related compounds. THCV is a non-psychoactive cannabinoid with structural similarity to THC that also acts on the endocannabinoid system. Laboratory and animal research show that it exhibits some anti-inflammatory effects. Presently most preferred cannabinoids include CBD, CBN and CBG.

Psychoactive cannabinoids such as tetrahydrocannabinol ("THC") are presently not preferred for a variety of reasons. Not only do those cannabinoids have psychoactive properties which may not be desired or appropriate for the circumstance, but they may also be subject to regulatory or labeling requirements that may limit their use. In addition, certain animals such as dogs do not tolerate psychoactive cannabinoids well. For example, THC has been reported to be toxic to dogs. For these reasons preferred compositions contain at most non-psychoactive amounts of THC, more preferably less than 0.3% THC, even more preferably less than 0.1%, yet more preferably less than 0.05% (500 ppm), most preferably less than 0.01% (100 ppm) and optimally less than 20 ppm, expressed as a percentage of the dry weight of the total *cannabis* extract.

*Cannabis* has been used medicinally for many years, and in Victorian times was a widely used component of prescription medicines. For example, *cannabis* was reportedly used as a hypnotic sedative for the treatment of hysteria, delirium, epilepsy, nervous insomnia, migraine, pain and dysmenorrhea. Historically, *cannabis* was regarded by many physicians as unique; having the ability to counteract pain resistant to opioid analgesics, in conditions such as spinal cord injury, and other forms of neuropathic pain including pain and spasm in multiple sclerosis.

The use of *cannabis* continued until the middle of the twentieth century, when the recreational use of *cannabis* prompted legislation which resulted in the prohibition of its use. The utility of *cannabis* as a prescription medicine is now being re-evaluated. The discovery of specific cannabinoid receptors and new methods of administration have made it possible to extend the use of *cannabis*-based medicines to some specific and in some cases novel indications.

The principle cannabinoid components present in herbal *cannabis* are the cannabinoid acids tetrahydrocannabinolic acid ("THCA") and cannabidiolic acid ("CBDA"), with small amounts of the corresponding neutral cannabinoids, respectively THC and CBD. Cannabidiol was formerly regarded as an inactive constituent, however there is evidence that it has pharmacological activity.

In addition to these major cannabinoids, herbal *cannabis* may contain lower levels of other minor cannabinoids.

These may be intermediates in the biosynthesis of the major cannabinoids and hence exist at only low levels in the plant as they are constantly undergoing further biotransformation once they are formed. An example of such a cannabinoid is CBG. Other minor cannabinoids may represent the end point of an alternative biosynthetic pathway to that leading to the formation of the major cannabinoids THC and CBD. These cannabinoids are frequently relatively more abundant in the plant, an example being CBC.

The so called "minor cannabinoids" can be present in greater (or even significantly greater) than normal proportions in selectively bred varieties of the herbal *cannabis* and hemp plants. The minor cannabinoids can also be isolated during processing, and mixtures of cannabinoids can be prepared having virtually any ratio of any particular cannabinoid.

In the case of the minor cannabinoids, past difficulties in isolating the minor cannabinoids in a pure state and the absence of commercially available standards have restricted the investigation of the pharmacology of these compounds.

Synthetic forms of certain of the cannabinoids, particularly CBD and CBN, are now commercially available. Presently, synthetic cannabinoids are rather expensive. Attention has therefore focused on the purification of cannabinoids from plant material.

In one effort, a process for preparing cannabinoids from plant material utilized $CO_2$ extraction and ethanol precipitation to obtain "primary extracts" of cannabinoids, with reduced amounts of monoterpenes, sesquiterpenes, hydrocarbons, alkaloids, flavonoids and chlorophylls. Other processes remove or isolate CBD and CBN using preparative gas chromatography.

*Cannabis* plants generally contain complex mixtures of cannabinoid acids and cannabinoids, although depending on the variety of *cannabis* one type of cannabinoid may predominate. The precise cannabinoid content of any particular *cannabis* plant material may be qualitatively and quantitatively determined using analytical techniques well known to those skilled in the art, such as thin-layer chromatography ("TLC") or high-performance liquid chromatography ("HPLC"). Thus, one may screen a range of *cannabis* plants and select those having a high content of the desired cannabinoid. A chromatographic step may be used to separate the various cannabinoid/cannabinoid acid components of the crude plant extract. Typically, the product of the chromatographic step is collected in multiple fractions, which may then be tested for the presence of the desired cannabinoid/cannabinoid acid using any suitable analytical technique (e.g., TLC). Fractions enriched in the desired cannabinoid/cannabinoid acid may then be selected for use or further purification.

Selectivity for different cannabinoids or cannabinoid acids may be enhanced by selection of appropriate starting plant material. By way of example, if it is desired to prepare substantially pure CBD or CBDA then "high CBD" *cannabis* plants should preferably be selected as the starting material. Using traditional selective breeding techniques manufacturers have been able to select *cannabis* varieties (chemovars) having a relatively high content of CBD, or of the minor cannabinoids such as CBG, CBC, CBN, CBE, CBL, etc. However, it is to be understood that the disclosed compositions are not limited to the use of particular *cannabis* varieties (chemovars) as the starting material.

Exemplary *cannabis* oils for use in the invention can contain neutral cannabinoids, acidic cannabinoids, and combinations thereof. Where it is desired to utilize neutral cannabinoids, rather than the corresponding cannabinoid acids, then a "decarboxylation" step can be used to decarboxylate cannabinoid acids to the corresponding neutral cannabinoid.

Examples of neutral cannabinoids include, but are not limited to: CBG and related compounds (e.g., cannabigerol monomethyl ether, cannabigerovarin); CBC and related compounds (e.g., cannabichromevarin); CBD and related compounds (e.g., cannabidiol monomethyl ether, cannabidiol-Ci, (−)-cannabidivarin, cannabidiorcol); CBND and related compounds (e.g., cannabinodivarin); CBN and related compounds (e.g., cannabinol-Ci, cannabivarin, cannabinol-C2, cannabiorcol, cannabinol methyl ether); CBT and related compounds (e.g., ethyl-cannabitriol, cannabitriol-C3); CBE and related compounds (e.g., cannabiglendol-C3, dehydrocannabifuran, cannabifuran); CBL and related compounds (e.g., cannabicyclovarin); CBT and related compounds; and CBCN and related compounds (e.g., cannabichromanone-C3, cannabicoumaronone). The structures of several neutral cannabinoids are set forth below.

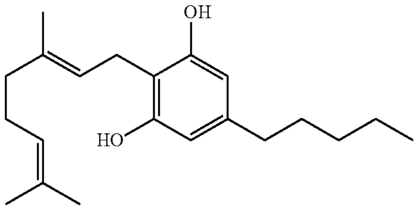

Cannabigerol [CBG]

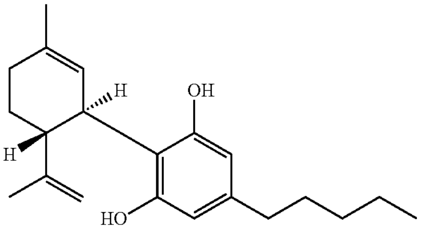

Cannabidiol [CBD]

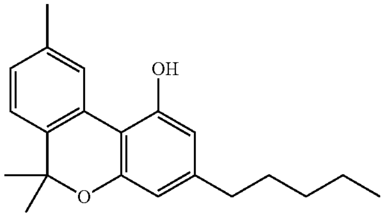

Cannabinol [CBN]

Examples of acidic cannabinoids include, but are not limited to: cannabigerolic acid A; cannabigerolic acid A monomethyl ether; cannabigerovarinic acid A; cannabichromenic acid A; cannabichromevarinic acid A; cannabidiolic acid; cannabidivarinic acid; cannabielsoic acid A; cannabielsoic acid B; C3-cannabielsoic acid B; and cannabicyclolic acid A.

The above-described techniques and other isolation, purification or synthetic techniques may be employed to prepare selected hemp extracts with optimum ratios of desired cannabinoids. These extracts (or isolates) may be combined with the above-mentioned active agents to provide the disclosed compositions, articles and method and achieve one or more health or wellness benefits. The cannabinoids may if desired be used with or without the aforementioned active agents. Thus in some embodiments, exemplary compositions contain a pharmacologically active amount of one or more cannabinoids, preferably CBD, and optionally CBD and at least a pharmacologically active amount of one or more minor cannabinoids.

Broad spectrum hemp extracts are preferably administered in a dosage of from 0.2 to 3, more preferably 0.3 to 2, and most preferably 0.4 to 1.2 mg per kg of body size.

The CBD ingredient is preferably administered in a dosage of from 0.1 to 2, more preferably 0.2 to 1.5, and most preferably 0.3 to 1 mg per kg of body size.

The CBN ingredient is preferably administered in a dosage of from up to 1, more preferably 0.1 to 0.5, and most preferably 0.1 to 0.3 mg per kg of body size.

The CBG ingredient is preferably administered in a dosage of from up to 1, more preferably 0.1 to 0.5, and most preferably 0.1 to 0.3 mg per kg of body size.

Exemplary active agents for use in, the disclosed compositions, articles and method include:

- amino acid-based ingredients that have central nervous system effects;
- receptor modulators for acetylcholinesterase, butyrylcholinesterase, 5-HT1 or 5-HT2;
- extracts or around portions (other than such receptor modulators) of certain medicinal plants, tree barks and roots; and
- monoamine metabolizers;
- other pharmacologically active chemicals, botanicals and agents.

Exemplary amino acid-based ingredients that have central nervous system effects include the first, second, and third active agents as discussed below.

A first active agent includes amino acid analogues of the proteinogenic amino acids L-glutamate and L-glutamine. Exemplary such compounds include D-theanine and L-theanine, with L-theanine being preferred. One commercially available and exemplary theanine is called SUNTHEANINE™, a generally pure L-isomer-theanine. Further information related to this compound can be found at www.suntheanine.com. Theanine's chemical structure is as follows:

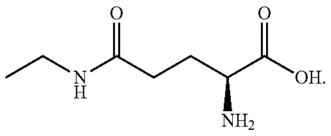

While not intending to be bound by theory, it is reported that theanine has central nervous system effects proposed to be inhibition of glutamate receptors, increasing the concentration of gamma aminobutyric acid (γ-aminobutyric acid or "GABA"), increasing dopamine and serotonin in specific brain regions, and inhibiting glutamate-induced effects, see DerMarderosian et al., Review of Natural Products 8th Edition (2014). Theanine is structurally similar to the excitatory neurotransmitter glutamate, and in accordance, binds to glutamate receptors. Specifically, it binds to ionotropic glutamate receptors in the micromolar range, including the α-amino-3-hydroxy-5-methyl-4-isoxazolepropionic acid ("AMPA") receptor and kainate receptors and, to a lesser extent, the N-methyl-D-aspartate ("NMDA") receptor. Theanine also binds to Group I metabotropic glutamate receptors ("mGluRs"). In addition, theanine inhibits glutamine transporters and glutamate transporters, and thus blocks the reuptake of glutamine and glutamate. While not intending to be bound by theory, theanine, as a structural analog of glutamate and glutamine, is believed to be absorbed in the small intestine after oral ingestion and to undergo hydrolysis to L-glutamate and ethylamine both in the intestine and liver. Theanine can also cross the blood brain barrier ("BBB") intact and register pharmacological effects directly, with effects evident within 30 minutes and measurable up to 5 hours after administration.

The theanine agent is preferably administered in a dosage of from 0.5 to 10, more preferably 1 to 7, and most preferably 1.5 to 5 mg per kg of body size.

A second active agent includes amino acids that attach to a protein in the brain known as a GABA receptor. Exemplary such compounds include GABA, whose chemical structure is as follows:

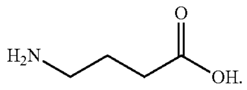

While not intending to be bound by theory, GABA is a naturally occurring amino acid that reportedly works as a neurotransmitter in the brain. Neurotransmitters function as chemical messengers. GABA is considered an inhibitory neurotransmitter because it blocks, or inhibits, certain brain signals and decreases nervous system activity.

The GABA agent is preferably administered in a dosage of from 1 to 20, more preferably 2 to 12, and most preferably 3 to 9 mg per kg of body size.

A third active agent comprises tryptophan (also called L-trytophan, L-trypt, L-2-amino-3-(indole-3-yl) propionic acid, or L-tryptophane) and related analogs such as 5-hydroxytryptophan ("5-HTP"). Tryptophan is an α-amino acid, a protein building block that can be found in many plant and animal proteins and which is used in the biosynthesis of proteins. Tryptophan contains an α-amino group, an α-carboxylic acid group, and a side chain indole, making it a non-polar aromatic amino acid. It is an essential amino acid in humans, meaning the body cannot synthesize it; it must be obtained from the diet. Tryptophan is also a precursor to the neurotransmitter serotonin, the hormone melatonin and vitamin B3. L-tryptophan's chemical structure is as follows:

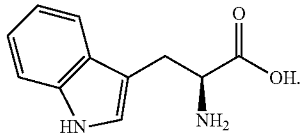 [SMILES: N[C@@H](Cc1c[nH]c2ccccc12)C(=O)O]

L-tryptophan is important for the development and functioning of many organs in the body. After absorbing L-tryptophan from food, the human body converts it to 5-HTP, and then to serotonin. Serotonin is a hormone that transmits signals between nerve cells. It also causes blood vessels to narrow.

The tryptophan agent is preferably administered in a dosage of from 1 to 20, more preferably 2 to 12, and most preferably 3 to 9 mg per kg of body size.

A fourth active agent includes compounds that modulate receptors for acetylcholinesterase, butyrylcholinesterase, or the serotonin (5-hydroxytryptamine or "5-HT") receptors 5-HT1 or 5-HT2. Exemplary such compounds include ashwagandha. A particularly preferred ashwagandha is SHODEN™ ashwagandha, which is described at www.nutriscienceusa.com/branded-ingredients/shoden-ashwagandha.

Ashwagandha is a plant and its root and berry are used to make medicine. The name Ashwagandha is from the Sanskrit language and is a combination of the word ashva, meaning horse, and gandha, meaning smell. The root has a strong aroma that is described as "horse-like." In Ayurvedic, Indian, and Unani medicine, ashwagandha is described as "Indian *ginseng*." Ashwagandha is also used in traditional African medicine for a variety of ailments.

While not intending to be bound by theory, it is reported that ashwagandha has central nervous systems effects, including modulation of acetylcholinesterase and butyrylcholinesterase activity, modulation of 5-HT1 and 5-HT2 receptors, antioxidant activity and regeneration of neurites. See *Review of Natural Products* 8*th Edition, id.*

The above-mentioned receptor modulators (e.g., ashwagandha) are preferably administered in a dosage of from 0.3 to 5, more preferably 0.6 to 4, and most preferably 1 to 3 mg per kg of body size.

A fifth active agent comprises one or more extracts or ground portions (other than the above-mentioned receptor modulators) of certain medicinal plants, tree barks and roots. A first bark useful as this agent is from the *Magnolia* plant (*Magnolia officinalis*). A second bark useful as this agent is from the *Phellodendron* plant (*Phellodendron amurense*). These two barks are medicinal plants that may be used separately or as a combination. *Magnolia* Bark Extract has been shown to decrease serotonin levels in the frontal cortex, hippocampus, striatum, hypothalamus, and nucleus accumbens. It is also believed to upregulate the cyclic adenosine monophosphate pathway. See *Review of Natural Products* 8*th Edition, id.*

A presently preferred combination of such barks is available as RELORA™ RELORA combines *Magnolia officinalis* with *Phellodendron amurense*. When used together, these tree barks are reported to support well-being and stress management, and may help balance the hypothalamic-pituitary-adrenal axis ("HPA axis"), which is a central hormone pathway of the body.

The medicinal plant, tree bark and root agent or agents (e.g., RELORA agent) are preferably administered in a dosage of from 2 to 30, more preferably 4 to 20, and most preferably 6 to 15 mg per kg of body size.

In some embodiments, a sixth active agent includes compounds that metabolize monoamines, as well as compounds that increase norepinephrine, dopamine, and serotonin levels in the body. One such compound is S-adenosyl methionine ("SAMe"). Other names for SAMe include ademetionine, adenosylmethionine, S-adenosyl-L-methionine, S-adenosylmethionine, S-adenosylmethionine butanedisulfonate, S-adenosylmethionine tosylate, S-adenosylmethionine tosylate disulfate, and SAM. SAMe's IUPAC name is (S)-2-amino-4-((SS)-(((2S,3S,4R,5R)-5-(6-amino-9H-purin-9-yl)-3,4-dihydroxytetrahydrofuran-2-yl)methyl) (methyl)sulfonio)butanoate, and its chemical structure is as follows:

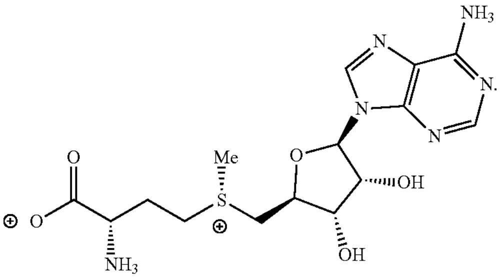 [SMILES: C[S@@+](CC[C@H](N)C(=O)[OH2+])C[C@H]1O[C@@H](n2cnc3c(N)ncnc32)[C@H](O)[C@@H]1O]

SAMe is a molecule formed naturally in the body, and can also be made in the laboratory. SAMe is involved in the formation, activation, or breakdown of other chemicals in the body, including hormones, proteins, phospholipids, and certain drugs. While not intending to be bound by theory, preclinical studies show that SAMe treatment affects monoamine metabolism, as well as increased norepinephrine, dopamine, and serotonin levels. See https://www.ncbi.nlm.nih.gov/pubmed/12418493; Mischolon, et. al. *Role of SAME in treatment of depression*, Am J Clin Nutr. 2002:76 (5):1158(s); Young, *Clinical nutrition:* 3. *The fuzzy boundary between nutrition and psychopharmacology*, CMAK 2002:166(2):205; Young, *The use of diet and dietary components in the study of/actors controlling affect in humans: a review*, J Psychiatry Neurosci. 1993:18(5):235-244; and Ravindran et al., *Complementary and alternative therapies as add-on to pharmacotherapy for mood and anxiety disorders: a systematic review*, J Affect Disord. 2013; 150:707-19. SAMe is reported to cross the intestinal wall, leading to increased plasma concentrations. Oral and parenteral forms of SAMe have been demonstrated to cross the blood-brain barrier and increase concentrations in cerebrospinal fluid, see *Review of Natural Products* 8th Edition., id.

The SAMe agent is preferably administered in a dosage of from 2 to 35, more preferably 4 to 25, and most preferably 6 to 17 mg per kg of body size.

In some embodiments, a seventh active agent comprises *ginseng*. *Ginseng* is the root of plants in the genus *Panax*, such as Korean *ginseng* (*P. ginseng*), South China *ginseng* (*P. notoginseng*), and American *ginseng* (*P. quinquefolius*), typically characterized by the presence of ginsenosides and gintonin. *Ginseng* has been used in traditional medicine and has been sold as a dietary supplement. The *ginseng* agent is preferably administered in a dosage of from 1 to 12, more preferably 1 to 9, and most preferably 2 to 6 mg per kg of body size.

In some embodiments, an eighth active agent comprises *Boswellia serrata*. *Boswellia serrata*, also known as Indian frankincense, is an herbal extract taken from the *Boswellia serrata* tree. *Boswellia* extract has been used in Asian and African folk medicine, and is reported to treat chronic inflammatory illnesses as well as a number of other health conditions. The *boswellia* agent is preferably administered in a dosage of from 1 to 20, more preferably 2 to 15, and most preferably 3 to 10 mg per kg of body size.

In some embodiments, a ninth active agent comprises turmeric. Turmeric is a flowering plant, *Curcuma longa* of the ginger family, Zingiberaceae. Plants are gathered each year for their rhizomes, which are used fresh or boiled in water and dried, after which they are around into a deep orange-yellow powder. Turmeric powder has a warm, bitter, black pepper-like flavor and earthy, mustard-like aroma. The turmeric agent is preferably administered in a dosage of from 4 to 60, more preferably 7 to 40, and most preferably 1 to 30 mg per kg of body size.

In some embodiments, a tenth active agent comprises methylsulfonylmethane ("MSM"). The biochemical effects of supplemental methylsulfonylmethane are not fully understood. Some researchers have suggested that MSM has anti-inflammatory effects. MSM is an organosulfur compound with the formula $(CH_3)_2SO_2$. It is also known by several other names including methyl sulfone and dimethyl sulfone ("DMSO2"). The MSM agent is preferably administered in a dosage of from 1 to 20, more preferably 2 to 15, and most preferably 4 to 10 mg per kg of body size.

As previously mentioned, exemplary compositions include: (i) one or more active agents; (ii) one or more cannabinoids; or (iii) a combination of one or more active agents and one or more cannabinoids. The compositions may further optionally comprise other ingredients (such as carriers, fillers, flavorants, flavor or taste masking agents, etc.) to provide the composition in a useful form factor.

While not intending to be bound by theory, it is presently believed that an individual's or animal's sleeplessness, anxiety or anxiousness, pain or inflammation can be caused by one or more of several different reasons. Consequently, a remedy having a single active ingredient may only address one pharmacological mechanism and may not be successful in addressing the individual's or animal's actual problem. Also, a single active ingredient composition may only address one of multiple causes that the individual or animal may have for a given problem. While not intending to be bound by theory, it is believed that a remedy having multiple active ingredients that can address multiple different potential causes or "triggers" for an issue will have a greater chance of success. For this reason, it is presently preferred to employ compositions and forms that contain several different active ingredients that treat a given problem from a variety of pathways. In this manner a more robust and general-purpose remedy can be provided. Consequently, exemplary compositions preferably contain two or more, preferably three or more, and most preferably four or more different active agents.

However, it is also desirable to avoid including ingredients that adversely interact with or inhibit one another. For example, if GABA is employed then it is desirable to avoid compositions containing significant amounts of GABA antagonists. Consequently, the disclosed compositions preferably contain no more than three, no more than two, no more than one or no active agents that adversely interact with or inhibit another active agent in the composition and thereby reduce its effectiveness for the composition's intended use in addressing sleeplessness, anxiety or anxiousness, pain or inflammation.

Preferred sleep aid compositions contain one or more cannabinoids (typically with an enhance amount of CBN) and one or more active agents selected from Relora, Ashwagandha and L-tryptophan.

For sleep aid products exemplary distillates preferably have an enhanced amount of CBN present (compared to typical broad-spectrum distillates), more preferably at least 1%, even more preferably at least 3% and even more preferably at least 5% CBN based on the distillate weight.

Preferred anti-anxiety compositions contain one or more cannabinoids (typically with an enhance amount of CBD) and one or more active agents selected from SAMe, GABA and 1-theanine).

For anxiety and wellness products exemplary distillates have between 50 and 100% CBD, more preferably between 70 and 95% CBD and most preferably between 80 to 90% CBD based on the distillate weight.

Preferred pain or anti-inflammatory compositions contain one or more cannabinoids (typically with an enhance amount of CBG) and one or more active agents selected from *boswellia* and MSM.

For pain or anti-inflammatory products, exemplary distillates preferably have an enhanced amount of CBG present (compared to typical broad-spectrum distillates), more preferably at least 3%, even more preferably at least 5% and yet more preferably at least 10% CBG based on the distillate weight.

In one embodiment, the disclosed compositions are provided in an ingestible form factor. Exemplary such ingestible form factors include chews, tablets, pills, melts, strips, toppers (or gravies), gums, gummies, shakes, bars, drinks and drink mixes, tinctures, and other foods. The ingestible form factor is preferably selected to meet the preferences of the mammal taking the ingestible composition. For example, a dog may in some cases prefer a hard or soft chew like that shown in FIG. 1. A human, in contrast, may prefer a melt strip like that shown in FIG. 3, a pill or capsule, or a food item. To prepare the ingestible form factor, the desired cannabinoid(s) and desired active agent(s) may be combined with other ingredients (generally non-active ingredients) and blended, mixed or layered as needed to form the final composition.

In another embodiment, the disclosed compositions are provided in a topically-applied form factor. Exemplary such topical form factors include lotions, shampoos, patches and roll-ons. The topical form factor is preferably selected to meet the preferences or needs of the mammal taking the composition. A patch, for example, may work very well on a human, but may not be appropriate for a furry dog. In any event, the topical form factor is constructed such that the active ingredients of the composition can be applied through the mammal's dermis. To create the topical form factor, the desired cannabinoid(s) and desired active agent(s) are combined with other ingredients (generally non-active ingredients) to form the final composition.

One illustrative topical composition is in the form of a lotion that contains typical known lotion ingredients such as natural or synthetic ceramides, essential fatty acids (e.g., olive oil, avocado, almond oil or shea butter), humectants (e.g., glycerin, glycols, polyols, sodium PCA), hyaluronic acid, aloe vera gel and other typical lotion adjuvants.

In another embodiment, the disclosed compositions are provided in a form factor that may be inhaled or otherwise introduced via the nose of a mammal. Exemplary such inhalable form factors include nasal sprays, inhalers, nettie pot solutions, vaporizers, smokable or smokeless compositions and other known inhalation devices.

In another embodiment, the disclosed compositions are provided in a form factor that may be introduced via the ear of a mammal. Exemplary such form factors include non-ototoxic, non-ciliotoxic ear drops and ear plugs.

In yet another embodiment, the disclosed compositions are provided in a food, or as an additive that may be applied to a food. For example, the composition may be in the form of a cookie, a bar, a gelatin, or a candy such as a gummy or other hard candy. In one illustrative embodiment the composition is provided as a "gravy-type" material loaded into a single use snap case form factor like that shown in FIG. 2. The single use snap case package preferably permits one-hand opening and easy dispensing of liquid and semi-liquid products. In one embodiment, the composition is for use by dogs, and the "gravy" (which contains a single dose of the active ingredients) is able to be easily applied to the dog's food, for example, or dispensed on the owner's palm and then consumed from the palm by the dog. A suitable package for use in this embodiment is available as the EASYSNAP™ container from Synchpack.

For use with animals, the disclosed compositions may also be applied to a toy device (e.g., applied to or soaked into) such as a bone, synthetic bone, plush toy, antler, rawhide chewable (which may be multilayered and have the composition as part of one or more of the layers), and the like. In one embodiment the disclosed compositions are contained in a chew resistant device that enables the composition to be licked over a prolonged period while resisting the animal's attempts to extricate the composition in a quick succession. This form factor is discussed further in copending U. S. Provisional. Application No. 63/13,108 filed Apr. 21, 2020 and in copending International Application No. PCT/US2021/028311 filed even date herewith, both of which are entitled PROLONGED INGESTION APPARATUS AND METHOD AND SYSTEM FOR USE and both of which are incorporated herein by reference.

In another embodiment the disclosed compositions are contained in an edible pet chew that enables the composition to be consumed over a prolonged period. This form factor is discussed further in copending U. S. Provisional. Application No. 63/13,103 filed Apr. 21, 2020 and in copending International Application No. PCT/US2021/028316 filed even date herewith, both of which are entitled EDIBLE PET CHEW TOY AND METHOD AND SYSTEM FOR USE and both of which are incorporated herein by reference.

The disclosed compositions and form factor articles may be used to treat or affect a wide variety of mammals. Exemplary mammals that can utilize the disclosed compositions and articles include humans, companion animals (e.g., dogs, cats, horses), zoo animals (gorillas, monkeys, etc.), and farm animals (e.g., cattle, cows, sheep, pigs, poultry, etc.).

A presently preferred approximate optimal dosage of the following active ingredients is shown below in Table 1:

TABLE 1

Approximate Optimal Dosage

| Ingredient | mg/kg |
|---|---|
| CBD | 0.6 |
| CBN | 0.2 |
| CBG | 0.2 |
| RELORA barks | 10 |
| SAMe | 12 |
| Tryptophan | 10 |
| GABA | 6 |
| Theanine | 3 |
| Ashwagandha | 2 |
| Turmeric | 21 |
| *Boswellia serrata* | 6 |
| Methylsulfonylmethane | 7 |
| Panax ginseng | 4 |
| 5-HTP | 5 |

The following examples are offered to aid in understanding of the present invention and are not to be construed as limiting the scope thereof. Unless otherwise indicated, all parts and percentages are by weight.

EXAMPLES

Example 1

Soft and Hard Chews

Exemplary ingestible soft chews were made by mixing 9.75 parts by weight of a blend of active agents (~61% SAMe, 17.5% GABA, 13.5% L-theanine and 8% Ashwagandha) with 0.35 parts by weight broad spectrum hemp oil and adjuvants that provide flavors, flavor masking, consistency and preservative properties, in the amounts shown below in Table 2:

TABLE 2

Exemplary Soft Chew Compositions

| Ingredient | Chicken Chew, Parts | Beef Chew, Parts |
|---|---|---|
| Chicken | 15.7 | |
| Beef liver | | 15.9 |
| Oat Flour | 15 | 15 |
| Potato Flakes, Fine Ground Idaho | 15 | 15 |
| Glycerin | 14 | 14 |
| Tapioca Starch | 12 | 12 |
| Sweet Potato, Powder | 5 | 5 |
| Sunflower Oil, Mid Oleic | 4 | 4 |
| Menhaden Fish Oil | 3 | 3 |
| Peanut Oil, High Roast | 3 | 3 |
| Flax Seed, Whole | 1.25 | 1.2 |
| Natural acidifiers | 1.5 | 1.5 |
| Lecithin, Dry | 0.25 | 0.3 |

Exemplary ingestible hard chews can be made using similar ingredients but with greater quantities of starch ingredients and without one or more of the softening ingredients such as glycerin. The resulting mixture can be converted using heat (e.g., baked) into a harder form factor.

Example 2

Gravy Toppers

An exemplary ingestible gravy topper was made from 15 parts of a blend of active agents (53.4 parts GABA, 43.3 parts L-theanine and 3.3 parts ashwagandha), with 0.7 parts broad spectrum hemp oil, 75 parts chicken bone broth, 7.3 parts fish oil and 2 parts flavoring.

Another exemplary ingestible gravy topper was made from 12 parts of a blend of active agents (160 parts GABA, 130 parts L-theanine and 10 parts ashwagandha), combined with 0.7 parts broad spectrum hemp oil, 75 parts chicken bone broth, 7.3 parts fish oil and 2 parts flavoring.

Another exemplary ingestible gravy topper can be made from 12 parts of a blend of active agents (160 parts GABA, 130 parts L-theanine and 10 parts ashwagandha), combined with 0.7 parts broad spectrum hemp oil, and 85 parts of typical gravy ingredients (e.g., a mixture of Chicken Bone Broth Powder, Natural Chicken Flavor, Natural Liver Flavor, Natural Cheddar Cheese Flavor, Natural Cream Flavor, Vegetable Glycerin, Water, Salt, Citric Acid, Sorbic Acid, Xanthan Gum, Rosemary Extract, and Lecithin.

Example 3

Melt Strips

An exemplary ingestible melt strip can be made using a blend of active agents (160 parts GABA, 130 parts L-theanine and 10 parts ashwagandha), combined with 0.7 parts broad spectrum hemp oil, together with dissolvable matrix materials as is known in the art.

Example 4

Blend of Four Active Agents

An exemplary batch of four active agents was prepared and assessed for efficacy. The batch contained the ingredient amounts shown below in Table 3:

TABLE 3

| Active Agent | Parts (by weight) |
|---|---|
| SAMe | 60.81 |
| GABA | 17.57 |
| L-theanine | 13.51 |
| Ashwagandha | 8.11 |

The four active agents were blended manually into a homogenous state and placed into 2-piece hard gelatin capsules, each containing approximately 390 mg of the four-ingredient blend.

The capsules were provided to human subjects for subjective evaluation of efficacy. One male and one female reported their results and impressions of the blend. Both subjects reported a perceived reduction in stress and anxious thoughts and emotions after ingesting the capsules. The male was a larger individual and ingested two capsules at a time, while the female ingested just one at a time. Both subjects also reported improved ability to concentrate under stressful conditions.

Example 5

Additional Blends of Four Active Agents

Batches of four active agents may be prepared containing amounts in the ranges shown below in Table 4. Lower and upper amounts are set out for each ingredient. Using amounts between the listed figures for each and any of the ingredients should maintain the general efficacy of the blends.

TABLE 4

| Active Agent | Parts, Low | Parts, High |
|---|---|---|
| SAMe | 30 | 70 |
| GABA | 10 | 40 |
| L-theanine | 5 | 20 |
| Ashwagandha | 4 | 12 |

The four active agents may be blended into a homogenous state and placed into a form factor for delivery to a subject. Preferably the chosen form factor contains approximately 400 mg of the four-ingredient blend. The capsules when administered to humans should provide a reduction in stress and anxious thoughts and emotions and improved ability to concentrate under stressful conditions.

Example 6

Blends of Three Active Agents

Batches of three active agents may be prepared containing amounts in the ranges shown below in Table 5. Lower and upper amounts are set out for each ingredient. Using amounts between the listed figures for each and any of the ingredients should maintain the general efficacy of the blends.

TABLE 6

| Active Agent | Parts, Low | Parts, High |
|---|---|---|
| GABA | 10 | 40 |
| L-theanine | 5 | 20 |
| Ashwagandha | 4 | 12 |

The three active agents may be blended into a homogenous state and placed into a form factor for delivery to a subject. Preferably the chosen form factor contains approximately 300 mg of the three-ingredient blend. The capsules when administered to humans should provide a reduction in stress and anxious thoughts and emotions and improved ability to concentrate under stressful conditions.

Example 7

Blend of Active Agents and CBD 97.5 Parts of the Example 1 agent blend were combined with 2.5 parts CBD, blended manually into a homogenous state and placed into 2-piece hard gelatin capsules. Each capsule contained approximately 400 mg of the five-ingredient blend. The capsules were provided to human subjects for subjective evaluation of efficacy. Two males and one female reported their results and impressions. All subjects reported better-quality sleep after ingesting the capsules. The male was a larger individual and ingested two capsules at a time, while the female ingested just one at a time. More specifically, the subjects reported more restful sleep and waking up in a non-groggy, refreshed state. One male and one female also reported decreased nerve pain (male: neck and shoulder; female: hip) that helped them fall asleep faster.

Example 8

Soft Chews with Active Agents and CBD

Soft chews were prepared for small, medium and large dogs. The treats contained the following active ingredients.

TABLE 8

| Ingredient | Small | Medium | Large |
|---|---|---|---|
| CBD | 5 mg | 10 mg | 15 mg |
| SAMe | 103 mg | 205 mg | 308 mg |
| GABA | 51 mg | 103 mg | 154 mg |
| L-theanine | 26 mg | 51 mg | 77 mg |
| Ashwagandha | 15 mg | 31 mg | 46 mg |

The chews were provided to dogs for subjective evaluation of efficacy and found to calm the dogs, reduce the dog's anxiety, and make them more focused when in training sessions.

The complete disclosure of all patents, patent applications, and publications, and electronically available material cited herein are incorporated by reference. The foregoing detailed description and examples have been given for clarity of understanding only. No unnecessary limitations are to be understood therefrom. The invention is not limited to the exact details shown and described, and variations obvious to one skilled in the art will be included within the invention defined by the claims. The invention illustratively disclosed herein suitably may be practiced, in some embodiments, in the absence of any element which is not specifically disclosed herein.

The invention claimed is:

1. A method for treating sleeplessness, anxiety or anxiousness, pain or inflammation in a companion animal, zoo animal or farm animal, the method comprising the step of administering to such animal a non-psychoactive composition comprising as active ingredients:

(i) one or more pharmacologically active, non-psychoactive cannabinoids; and (ii) a pharmacologically active, non-prescription, non-cannabinoid active agent from each of the following subclasses:

a) amino acid-based ingredients having central nervous system effects;

b) receptor modulators for acetylcholinesterase, butyrylcholinesterase, 5-HT1 or 5-HT2; and c) extracts or ground portions (other than such receptor modulators) of a medicinal plant, tree bark or roots; and (iii) an optional carrier or matrix in which active ingredients (i) and (ii) are dispersed.

2. The method of claim 1, wherein the animal is a companion animal.

3. The method of claim 2, wherein the animal is a dog.

4. The method of claim 2, wherein the animal is a cat.

5. The method of claim 1, wherein the animal is a farm animal.

6. The method of claim 1, wherein the composition is in the form of an article comprising the carrier or matrix in which active ingredients (a) and (b) are dispersed, and wherein the carrier or matrix comprises a chew resistant device that enables the active ingredients to be consumed over a prolonged period.

7. The method of claim 1, wherein the composition contains the carrier or matrix and the carrier or matrix comprises a solvent, dispersing liquid, dissolvable support, solid support, filler, flavorant, flavor or taste masking agent, and other adjuvants that provide the composition in the useful form factor.

8. The method of claim 1, wherein the composition contains the carrier or active matrix.

9. The method of claim 8, further comprising a nonprescription active agent from the following subclass:

d) monoamine metabolizers.

10. The method of claim 8, wherein the composition contains the carrier or matrix and the carrier or matrix comprises a solvent, dispersing liquid, dissolvable support, solid support, filler, flavorant, flavor or taste masking agent, and other adjuvants that provide the composition in the useful form factor.

11. The method of claim 8, wherein the composition is free of prescription drugs.

12. The method of claim 8, wherein the composition is free of over-the-counter cold remedies.

13. The method of claim 8, wherein the composition is free of over-the-counter allergy treatments.

14. The method of claim 8, wherein the composition is free of stimulants.

15. The method of claim 8, wherein the composition is free of antagonists for the amino acid-based ingredients present in the composition.

16. The method of claim 8, wherein the composition is free of antagonists for the receptor modulators present in the composition.

17. The method of claim 8, wherein the composition is free of antagonists for the extracts of a medicinal plant, tree bark or root present in the composition.

18. The method of claim 8, wherein the composition contains no more than three active agents that adversely interact with or inhibit another active agent in the composition and thereby reduce its effectiveness in treating sleeplessness, anxiety or anxiousness, pain or inflammation.

19. The method of claim 8, wherein the composition contains no more than two active agents that adversely interact with or inhibit another active agent in the composition and thereby reduce its effectiveness in treating sleeplessness, anxiety or anxiousness, pain or inflammation.

20. The method of claim 8, wherein the composition contains no more than one active agent that adversely interacts with or inhibits another active agent in the composition and thereby reduces its effectiveness in treating sleeplessness, anxiety or anxiousness, pain or inflammation.

21. The method of claim 8, wherein the composition contains no active agents that adversely interact with or inhibit another active agent in the composition and thereby reduce its effectiveness in treating sleeplessness, anxiety or anxiousness, pain or inflammation.

22. The method of claim 8, wherein the composition comprises cannabidiol ("CBD").

* * * * *